US010100330B2

(12) United States Patent
Bowen et al.

(10) Patent No.: US 10,100,330 B2
(45) Date of Patent: Oct. 16, 2018

(54) INSECT INHIBITORY PROTEINS

(71) Applicant: Monsanto Technology LLC, St. Louis, MO (US)

(72) Inventors: David J. Bowen, Chesterfield, MO (US); Catherine A. Chay, Ballwin, MO (US); Stanislaw Flasinski, Chesterfield, MO (US); Yong Yin, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/221,544

(22) Filed: Jul. 27, 2016

(65) Prior Publication Data

US 2017/0044568 A1 Feb. 16, 2017

Related U.S. Application Data

(60) Provisional application No. 62/199,024, filed on Jul. 30, 2015.

(51) Int. Cl.

| | |
|---|---|
| ***C12N 15/82*** | (2006.01) |
| ***C07K 14/325*** | (2006.01) |
| ***A01N 37/46*** | (2006.01) |
| ***A01N 63/02*** | (2006.01) |
| *C12Q 1/6897* | (2018.01) |

(52) U.S. Cl.

CPC ......... *C12N 15/8286* (2013.01); *A01N 37/46* (2013.01); *A01N 63/02* (2013.01); *C07K 14/325* (2013.01); *C12Q 1/6897* (2013.01); *Y02A 40/162* (2018.01)

(58) Field of Classification Search

None

See application file for complete search history.

(56) References Cited

U.S. PATENT DOCUMENTS

| | | | |
|---|---|---|---|
| 6,066,783 A * | 5/2000 | Warren .................. | A01N 63/00 435/252.3 |
| 6,551,962 B1 | 4/2003 | Pershing et al. | |
| 7,510,878 B2 | 3/2009 | Abad et al. | |
| 7,772,465 B2 | 8/2010 | Abad et al. | |
| 7,812,129 B1 | 10/2010 | Abad et al. | |
| 8,129,593 B2 | 3/2012 | Abad et al. | |
| 8,283,524 B2 | 10/2012 | Abad et al. | |
| 8,445,749 B2 | 5/2013 | Abad et al. | |
| 8,586,832 B2 | 11/2013 | Abad et al. | |
| 8,692,065 B2 | 4/2014 | Abad et al. | |
| 8,772,577 B2 | 7/2014 | Abad et al. | |
| 8,802,934 B2 | 8/2014 | Abad et al. | |
| 8,822,762 B2 | 9/2014 | Liu et al. | |
| 2006/0021087 A1 | 1/2006 | Baum et al. | |
| 2010/0077507 A1 | 3/2010 | Abad et al. | |
| 2012/0278954 A1 | 11/2012 | Bowen et al. | |
| 2013/0055469 A1 | 2/2013 | Sampson et al. | |
| 2013/0097735 A1 | 4/2013 | Bowen et al. | |
| 2013/0227743 A1 | 8/2013 | Grandlic et al. | |
| 2015/0047076 A1 | 2/2015 | Anderson et al. | |

OTHER PUBLICATIONS

Palma et al, 2014, Toxins, 6:3296-3325.*
Geng et al, 2013, GenBank accession AEB52299.1.*
Feldgarden et al, 2012, GenBank accession EJS10693.*
Ammons et al, 2013, GenBank accession AGT29561.1.*
Argolo-Filho et al, 2014, Insects 5:62-91.*
James, "Global Status of Commercialized Biotech/GM Crops: 2012," ISAAA Brief No. 44.
GenBank Accession No. KC960015, dated Aug. 18, 2013.
International Search Report and Written Opinion regarding International Application No. PCT/US2016/044296, dated Oct. 25, 2016.
De Maagd et al., "Structure, Diversity, and Evolution of Protein Toxins from Spore-Forming Entomopathogenic Bacteria," *Annu. Rev. Genet.* 37:409-433, 2003.
Bart et al., "Binary Bacterial Toxins: Biochemistry, Biology, and Applications of Common *Clostridium* and *Bacillus* Proteins," *Microbiol. Mol. Biol. Rev.* 68(3):373-402, 2004.

* cited by examiner

*Primary Examiner* — Anne Kubelik

(74) *Attorney, Agent, or Firm* — Dentons US LLP; Timothy K. Ball, Esq.; Carine M. Doyle, Esq.

(57) ABSTRACT

A pesticidal protein class exhibiting toxic activity against Coleopteran, Lepidopteran, and Hemipteran pest species is disclosed, and includes, but is not limited to, TIC5290. DNA constructs are provided which contain a recombinant nucleic acid sequence encoding the TIC5290 pesticidal protein. Transgenic plants, plant cells, seed, and plant parts resistant to Lepidopteran, Coleopteran and Hemipteran infestation are provided which contain recombinant nucleic acid sequences encoding the TIC5290 pesticidal protein of the present invention. Methods for detecting the presence of the recombinant nucleic acid sequences or the protein of the present invention in a biological sample, and methods of controlling Coleopteran, Lepidopteran, and Hemipteran species pests using the TIC5290 pesticidal protein are also provided.

26 Claims, 1 Drawing Sheet

Specification includes a Sequence Listing.

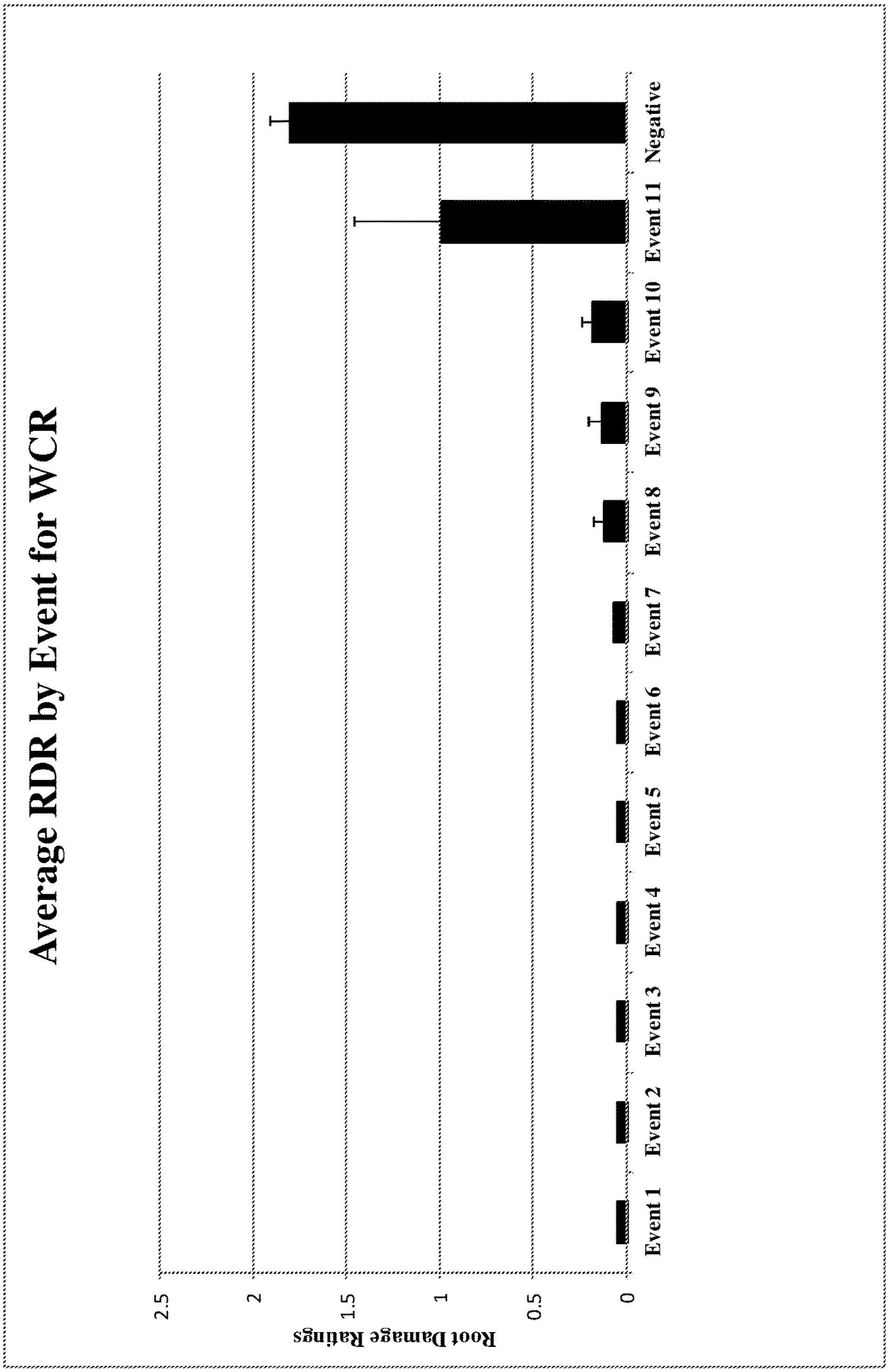
Average RDR by Event for WCR
Root Damage Ratings
2.5
2
1.5
1
0.5
0
Event 1
Event 2
Event 3
Event 4
Event 5
Event 6
Event 7
Event 8
Event 9
Event 10
Event 11
Negative

INSECT INHIBITORY PROTEINS

REFERENCE TO RELATED APPLICATION

This application claims the benefit of U.S. Provisional Application No. 62/199,024, filed Jul. 30, 2015, which is herein incorporated by reference in its entirety.

INCORPORATION OF SEQUENCE LISTING

The file named "MONS394US_sequence_listing.txt" containing a computer-readable form of the Sequence Listing was created on Jul. 19, 2016. This file is 16,077 bytes (measured in MS-Windows®), is contemporaneously filed by electronic submission (using the United States Patent Office EFS-Web filing system), and is incorporated into this application by reference in its entirety.

FIELD OF THE INVENTION

The invention generally relates to the field of insect inhibitory proteins. A novel class of proteins exhibiting insect inhibitory activity against agriculturally-relevant pests of crop plants and seeds is disclosed. In particular, the disclosed protein is insecticidally active against agriculturally-relevant pests of crop plants and seeds, particularly Coleopteran, Lepidopteran, and Hemipteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the Lepidoptera, Coleoptera and Hemipteran orders, are considered a major cause of damage to field crops, thereby decreasing crop yields over infested areas. Lepidopteran pest species which negatively impact agriculture include, but are not limited to, *Helicoverpa zea, Ostrinia nubilalis, Diatraea saccharalis, Diatraea grandiosella, Anticarsia gemmatalis, Spodoptera frugiperda, Spodoptera exigua, Agrotis ipsilon, Trichoplusia ni, Chrysodeixis includens, Heliothis virescens, Plutella xylostella, Pectinophora gossypiella, Helicoverpa armigera, Elasmopalpus lignosellus, Striacosta albicosta and Phyllocnistis citrella*. Coleopteran pest species which negatively impact agriculture include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly wherein the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica undecimpunctata howardii* (Southern Corn Rootworm, SCR), and a Brazilian Corn Rootworm complex (BCR) consisting of *Diabrotica viridula* and *Diabrotica speciosa*). Hemipteran pest species which negatively impact agriculture include, but are not limited to, *Lygus hesperus, Lygus lineolaris*, and *Pseudatomoscelis seriatus.*

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*) and *Paenibacillus popilliae.*

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus the inventors herein disclose a novel protein toxin family from *Bacillus thuringiensis* along with similar toxin proteins, variant proteins, and exemplary recombinant proteins that exhibit insecticidal activity against target Lepidopteran, Coleopteran and Hemipteran pest species, particularly against Western Corn Rootworm.

SUMMARY OF THE INVENTION

Disclosed herein is a novel group of pesticidal proteins with insect inhibitory activity (toxin proteins), referred to herein as TIC5290, which are shown to exhibit inhibitory activity against one or more pests of crop plants. The TIC5290 protein and proteins in the TIC5290 protein toxin class can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or fragment thereof, wherein: (a) said pesticidal protein comprises the amino acid sequence of SEQ ID NO:2; or (b) said pesticidal protein comprises an amino acid sequence having at least 65%, or 70%, or 75%, or 80%, or 85%, or 90%, or 95%, or 98%, or 99% or about 100% amino acid sequence identity to SEQ ID NO:2; or (c) said polynucleotide segment hybridizes to a polynucleotide having the nucleotide sequence of SEQ ID NO:1 or SEQ ID NO:3; or (d) said polynucleotide segment encoding a pesticidal protein or fragment thereof comprises a polynucleotide sequence having at least 65%, or 70%, or 75%, or 80%, or 85%, or 90%, or 95%, or 98%, or 99% or about 100% sequence identity to the nucleotide sequence of SEQ ID NO:1 or SEQ ID NO:3; or (e) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application are host cells comprising a recombinant nucleic acid molecule of the application, wherein the host cell is selected from the group consisting of a bacterial and a plant cell. Contemplated host cells include *Agrobacterium, Rhizobium, Bacillus, Brevibacillus, Escherichia, Pseudomonas, Klebsiella, Pantoea*, and *Erwinia*. In certain embodiments said *Bacillus* species is *Bacillus cereus* or *Bacillus thuringiensis*, said *Brevibacillus* is *Brevibacillus laterosperus*, or said *Escherichia* is *Escherichia coli*. Contemplated plant host cells include a dicotyledonous cell and a monocotyledonous cell. Further contemplated plant host cells include an alfalfa, banana, barley, bean, broccoli, cabbage, *Brassica*, carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In yet another embodiment, the pesticidal protein exhibits activity against Coleopteran insect, including Western Corn Rootworm, Southern Corn Rootworm, Northern Corn Rootworm, Mexican Corn Rootworm, Brazilian Corn Rootworm, or Brazilian Corn Rootworm complex consisting of *Diabrotica viridula* and *Diabrotica speciosa*.

In another embodiment, the pesticidal protein exhibits activity against a Lepidopteran insect, including Velvet bean caterpillar, Sugarcane borer, Lesser cornstalk borer, Corn earworm, Tobacco budworm, Soybean looper, Black armyworm, Southern armyworm, Fall armyworm, Beet armyworm, Old World bollworm, Oriental leaf worm, Pink bollworm, Black cutworm, Southwestern Corn Borer, Diamondback moth, or European corn borer.

In yet another embodiment, the pesticidal protein exhibits activity against a Hemipteran insect, including Western tarnished plant bug, Tarnished plant bug, or Cotton fleahopper.

Also contemplated in this application are plants comprising a recombinant nucleic acid molecule comprising a heterologous promoter operably linked to a polynucleotide segment encoding a pesticidal protein or fragment thereof, wherein: (a) said pesticidal protein comprises the amino acid sequence of SEQ ID NO:2; or (b) said pesticidal protein comprises an amino acid sequence having at least 65%, or 70%, or 75%, or 80%, or 85%, or 90%, or 95%, or 98%, or 99%, or about 100% amino acid sequence identity to SEQ ID NO:2; or (c) said polynucleotide segment hybridizes under stringent hybridization conditions to the compliment of the nucleotide sequence of SEQ ID NO:1 or SEQ ID NO:3; or (d) said plant exhibits a detectable amount of said pesticidal protein. In certain embodiments the pesticidal protein comprises SEQ ID NO:2. In one embodiment, the plant is either a monocot or a dicot. In another embodiment, the plant is selected from the group consisting of an alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. The at least one other pesticidal agent is selected from the group consisting of an insect inhibitory protein, an insect inhibitory dsRNA molecule, and an ancillary protein. The at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of: a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657 and a DIG-11protein.

Commodity products comprising a detectable amount of the recombinant nucleic acid molecules disclosed in this application are contemplated. Such commodity products include commodity corn bagged by a grain handler, corn flakes, corn cakes, corn flour, corn meal, corn syrup, corn oil, corn silage, corn starch, corn cereal, and the like, and corresponding cotton commodity products such as whole or processed cotton seed, cotton oil, lint, seeds and plant parts processed for feed or food, fiber, paper, biomasses, and fuel products such as fuel derived from cotton oil or pellets derived from cotton gin waste, and corresponding soybean commodity products such as whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts, and corresponding rice, wheat, sorghum, pigeon pea, peanut, fruit, melon, and vegetable commodity products including where applicable, juices, concentrates, jams, jellies, marmalades, and other edible forms of such commodity products containing a detectable amount of such polynucleotides and or polypeptides of this application.

Also contemplated in this application is a method of producing seed comprising the recombinant nucleic acid molecules disclosed in this application. The method comprises planting at least one of the seed comprising the recombinant nucleic acid molecules disclosed in this application; growing plant from the seed; and harvesting seed from the plants, wherein the harvested seed comprises the recombinant nucleic acid molecules in this application.

In another illustrative embodiment, a plant resistant to insect infestation is provided, wherein the cells of said plant comprise: (a) a recombinant nucleic acid molecule encoding an insecticidally effective amount of a pesticidal protein as set forth in SEQ ID NO:2; or (b) an insecticidally effective amount of a protein comprising an amino acid sequence having at least 65%, or 70%, or 75%, or 80%, or 85%, or 90%, or 95%, or about 100% amino acid sequence identity to SEQ ID NO:2.

Also disclosed in this application are methods for controlling a Coleopteran or Lepidopteran or Hemipteran species pest, and controlling a Coleopteran or Lepidopteran or Hemipteran species pest infestation of a plant, particularly a crop plant. The method comprises, in one embodiment, (a) contacting the pest with an insecticidally effective amount of one or more pesticidal proteins as set forth in SEQ ID NO:2; or (b) contacting the pest with an insecticidally effective amount of one or more pesticidal proteins comprising an amino acid sequence having at least 65%, or 70%, or 75%, or 80%, or 85%, or 90%, or 95%, or about 100% amino acid sequence identity to SEQ ID NO:2.

Further provided herein is a method of detecting the presence of a recombinant nucleic acid molecule comprising a polynucleotide segment encoding a pesticidal protein or fragment thereof, wherein: (a) said pesticidal protein comprises the amino acid sequence of SEQ ID NO:2; or (b) said pesticidal protein comprises an amino acid sequence having at least 65%, or 70%, or 75%, or 80%, or 85%, or 90%, or 95%, or 98%, or 99%, or about 100% amino acid sequence identity to SEQ ID NO:2; or (c) said polynucleotide segment hybridizes to a polynucleotide having the nucleotide sequence of SEQ ID NO:1 or SEQ ID NO:3. In one embodiment of the invention, the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NO:1, SEQ ID NO:3, or a sequence that encodes a pesticidal protein comprising an amino acid sequence having at least 65%, or 70%, or 75%, or 80%, or 85%, or 90%, or 95%, or 98%, or 99%, or about 100% amino acid sequence identity to SEQ ID NO:2. The method may further comprise (a) subjecting the sample and probe to stringent hybridization conditions; and (b) detecting hybridization of the probe with DNA of the sample.

Also provided by the invention are methods of detecting the presence of a pesticidal protein or fragment thereof in a sample comprising protein, wherein said pesticidal protein comprises the amino acid sequence of SEQ ID NO:2; or said pesticidal protein comprises an amino acid sequence having at least 65%, or 70%, or 75%, or 80%, or 85%, or 90%, or 95%, or 98%, or 99%, or about 100% amino acid sequence identity to SEQ ID NO:2. In one embodiment, the method comprises: (a) contacting a sample with an immunoreactive antibody; and (b) detecting the presence of the protein. In some embodiments the step of detecting comprises an ELISA, or a Western blot.

BRIEF DESCRIPTION OF THE DRAWINGS

FIG. 1 illustrates in planta Western Corn Rootworm (WCR) inhibitory activity of exemplary chloroplast targeted and non-targeted TIC5290 proteins.

BRIEF DESCRIPTION OF THE SEQUENCES

SEQ ID NO:1 is a nucleic acid encoding a TIC5290 pesticidal protein sequence obtained from *Bacillus thuringiensis* species EG6657.

SEQ ID NO:2 is the amino acid sequence of the TIC5290 protein.

SEQ ID NO:3 is a synthetic coding sequence encoding a TIC5290 pesticidal protein used for expression in plant cells.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel insecticidal proteins are disclosed herein, exemplified by TIC5290 and related family members that provide resistance against Coleopteran, Lepidopteran, and Hemipteran insect pests, and more particularly against corn rootworm pest species. Also disclosed are synthetic coding sequences designed for expression in a plant cell that encode TIC5290. Further disclosed are recombinant nucleic acid molecules comprising a promoter in operable linkage to a coding sequence encoding a TIC5290 toxin protein, or related family members, or fragments thereof.

Reference in this application to TIC5290, "TIC5290 protein", "TIC5290 protein toxin", "TIC5290 toxin protein", "TIC5290 pesticidal protein", "TIC5290-related toxins", or "TIC5290-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC5290 (SEQ ID NO:2) and pesticidal or insect inhibitory segments thereof, or combinations thereof, that confer activity against Coleopteran pests, Lepidopteran pests, and Hemipteran pests, including any protein exhibiting pesticidal or insect inhibitory activity if alignment of such protein with TIC5290 results in amino acid sequence identity of any fraction percentage from about 65 to about 100 percent.

The term "segment" or "fragment" is used in this application to describe consecutive amino acid or nucleic acid sequences that are shorter than the complete amino acid or nucleic acid sequence describing the TIC5290 protein or related family member insecticidal protein. A segment or fragment exhibiting insect inhibitory activity is also disclosed in this application if alignment of such segment or fragment, with the corresponding section of the TIC5290 protein set forth in SEQ ID NO:2, results in amino acid sequence identity of any fraction percentage from about 65 to about 100 percent between the segment or fragment and the corresponding section of the TIC5290 protein.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC5290 protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera, Coleoptera or Hemiptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include, but are not limited to, dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopteran, Coleopteran and Hemipteran pest species, as well as protein toxins that are used to control other plant pests such as Cry proteins available in the art for use in controlling Homopteran species.

It is intended that reference to a pest, particularly a pest of a crop plant, means insect pests of crop plants, particularly those that are controlled by the TIC5290 protein. However, reference to a pest can also include Homopteran insect pests of plants, as well as nematodes and fungi when toxic agents targeting these pests are co-localized or present together with the TIC5290 protein, or a protein that is about 65 to about 100 percent identical to TIC5290.

The insecticidal proteins of the TIC5290 protein toxin class are related by common function and exhibit insecticidal activity towards insect pests from the Coleopteran and Lepidopteran insect species, including adults, pupae, larvae, and neonates, as well as Hemipteran insect species, including adults and nymphs.

The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), Southern armyworm (*Spodoptera eridania*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Ho-*

*moeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), surgarcane borer (*Diatraea* saccharalis), spiny bollworm (*Earias insulana*), spotted bollworm (*Earias vittella*), Old World bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), diamondback moth (*Plutella xylostella*), beet armyworm (*Spodoptera exigua*), tobacco cutworm (*Spodoptera litura*, also known as cluster caterpillar), and tomato leafminer (*Tuta absoluta*).

The insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly when the pest is Western Corn Rootworm (*Diabrotica virgifera*, WCR), Northern Corn Rootworm (*Diabrotica barberi*, NCR), Mexican Corn Rootworm (*Diabrotica virgifera zeae*, MCR), Brazilian Corn Rootworm (*Diabrotica balteata*, BZR), Southern Corn Rootworm (*Diabrotica undecimpunctata howardii*, SCR) and a Brazilian Corn Rootworm complex (BCR, consisting of *Diabrotica viridula* and *Diabrotica speciosa*).

The insects of Hemiptera include, but are not limited to, Western tarnished plant bug (*Lygus hesperus*), Tarnished plant bug (*Lygus lineolaris*), and Cotton fleahopper (*Pseudatomoscelis seriatus*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further herein, an open reading frame (ORF) encoding TIC5290 (SEQ ID NO:1), was discovered in DNA obtained from *Bacillus thuringiensis* strain EG6657. The coding sequence was cloned and expressed in microbial host cells to produce protein (SEQ ID NO:2) used in bioassays. The closest toxin homolog to TIC5290 is the Vip4Aa protein with a sequence identity of 56.9%, indicating that TIC5290 represents a novel Vip4 subfamily. Bioassay using microbial host cell-derived proteins of TIC5290 demonstrated activity against the Coleopteran pest Western Corn Rootworm (*Diabrotica virgifera virgifera*, WCR); the Lepidopteran species Fall armyworm (*Spodoptera frugiperda*, FAW), Corn earworm (*Helicoverpa zea*, CEW), European corn borer (*Ostrinia nubilalis*), and Diamondback moth (*Plutella xylostella*); as well as the Hemipteran pest Western tarnished plant bug (*Lygus hesperus*).

It is contemplated that additional toxin protein sequences related to TIC5290 can be created by using the naturally occurring amino acid sequence of TIC5290 to create novel proteins and with novel properties. The TIC5290 toxin protein can be aligned with other proteins similar to TIC5290 to combine differences at the amino acid sequence level into novel amino acid sequence variants and making appropriate changes to the recombinant nucleic acid sequence encoding the variants.

It is further contemplated that improved variants of TIC5290 can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of the TIC5290 protein or protein variants thereof can be truncated forms wherein one or more amino acids are deleted from the N-terminal end, C-terminal end, the middle of the protein, or combinations thereof with insect inhibitory activity. These fragments can be naturally occurring or synthetic variants of TIC5290 or derived protein variants, but should retain the insect inhibitory activity of TIC5290.

Proteins that resemble the TIC5290 protein can be identified by comparison to each other using various computer based algorithms known in the art. For example, amino acid sequence identities of proteins related to TIC5290 can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran, Coleopteran or Hemipteran insect species is related to TIC5290 if alignment of such query protein with TIC5290 exhibits at least 65% to about 100% amino acid identity along the length of the query protein that is about 65%, 66%, 67%, 68%, 69%, 70%, 75%, 76%, 77%, 78%, 79%, 80%, 81%, 82%, 83%, 84%, 85%, 85%, 87%, 88%, 89%, 90%, 91%, 92%, 93%, 94%, 95%, 96%, 97%, 98%, 99%, 100% amino acid sequence identity (or any fraction of a percentage in this range) between query and subject protein.

The TIC5290 protein can also be related by primary structure (conserved amino acid motifs), by length (about 937 amino acids) and by other characteristics. Bioinformatic analysis suggests that TIC5290 is a pore-forming protein, has a PA14 Pfam domain (PF07691) that is likely involved with binding functions to cell receptor(s) on the target insect midgut is detected in amino acids 16-140, followed by a Binary_toxB Pfam domain (PF03495) in amino acids 186-593 that might contribute to the formation of a beta barrel transmembrane pore. Both of these Pfams likely contribute to insecticidal activity of the protein. Characteristics of the TIC5290 protein toxin are reported in Table 1.

transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express TIC5290 and demonstrate pesticidal activity through bioassays performed in the presence of Lepidoptera or Hemiptera pest larvae using plant leaf disks obtained from transformed plants. To test pesticidal activity against Coleopteran pests, transformed plants of $R_o$ and $F_1$ generation are used in root worm assay as described in the example below.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. As understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombina-

TABLE 1

Selected characteristics of the TIC5290 protein.

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| TIC5290 | 104962.93 | 937 | 6.7076 | 1.0 | 116 | 110 | 440 | 497 |

As described further in the Examples of this application, recombinant nucleic acid molecule sequences encoding TIC5290 were designed for use in plants. An exemplary plant-optimized recombinant nucleic acid molecule sequence that was designed for use in plants encoding the TIC5290 protein is set forth in SEQ ID NO:3.

Expression cassettes and vectors containing these synthetic nucleic acid molecule sequences can be constructed and introduced into corn, soybean, cotton or other plant cells in accordance with transformation methods and techniques known in the art. For example, *Agrobacterium*-mediated tion, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode TIC5290 are contemplated. For example, TIC5290 protein can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the TIC5290 protein encoding sequences for expression of the protein in plants or a Bt-functional promoter operably linked to a TIC5290 protein encoding sequence for expression of the protein in a Bt bacterium or other *Bacillus* species. Other elements can be operably linked to the TIC5290 protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:1 and SEQ ID NO:3 that encodes the polypeptide or protein having the amino acid sequence as set forth in SEQ ID NO:2. A heterologous promoter can also be operably linked to synthetic DNA coding sequences encoding a plastid targeted TIC5290 and untargeted TIC5290. The codons of a recombinant nucleic acid molecule encoding for protein disclosed herein can be substituted by synonymous codons (known in the art as a silent substitution).

A recombinant DNA construct comprising a TIC5290 protein encoding sequence can further comprise a region of DNA that encodes for one or more insect inhibitory agents which can be configured to concomitantly express or co-express with a DNA sequence encoding a TIC5290 protein, a protein different from a TIC5290 protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which TIC5290 is expressed from a common nucleotide segment which also contains other open reading frames and promoters, depending on the type of expression system selected. For example, a plant multi-gene expression system can utilize a single promoter to drive expression of multiply-linked/tandem open reading frames from within a single operon. In another example, a plant multi-gene expression system can utilize multiply-unlinked expression cassettes each expressing a different protein or other agent such as one or more dsRNA molecules.

Recombinant nucleic acid molecules or recombinant DNA constructs comprising a TIC5290 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC5290 protein encoding sequence in a host cell, or subsequent expression of the encoded polypeptide. An exogenous recombinant polynucleotide or recombinant DNA construct that comprises a TIC5290 protein encoding sequence and that is introduced into a host cell is referred herein as a "transgene".

Transgenic bacteria, transgenic plant cells, transgenic plants, and transgenic plant parts that contain a recombinant polynucleotide that expresses any one or more of the TIC5290 protein encoding sequences are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Coleoptera-, or Lepidoptera-, or Hemiptera-inhibitory amounts of a TIC5290 protein are provided. Such plants can be made by introducing a recombinant polynucleotide that encodes the TIC5290 protein provided in this application into a plant cell, and selecting a plant derived from said plant cell that expresses an insect, Coleoptera-, or Lepidoptera-, or Hemiptera-inhibitory amount of the TIC5290 protein. Plants can be derived from the plant cells by regeneration, seed, pollen, or meristem transformation techniques. Methods for transforming plants are known in the art.

Processed plant products, wherein the processed product comprises a detectable amount of a TIC5290 protein, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC5290 protein.

Plants expressing the TIC5290 protein can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

As described further in the Examples, synthetic or artificial sequences encoding TIC5290 that were designed for use in plants are set forth in SEQ ID NO:3.

For expression in plant cells, the TIC5290 protein can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the choloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442, 1987) or the *Petunia hybrida* EPSPS CTP (CTP4) (See, della-Cioppa et al., *Proc. Natl. Acad. Sci. USA* 83:6873-6877, 1986) has been shown to target heterologous EPSPS protein sequences to chloroplasts in transgenic plants (See, U.S. Pat. Nos. 5,627,061; 5,633,435; and 5,312,910; and EP 0218571; EP 189707; EP 508909; and EP 924299). For targeting the TIC5290 protein to the chloroplast, a sequence encoding a chloroplast transit peptide is placed 5' in operable linkage and in frame to a synthetic coding sequence encoding the TIC5290 toxin protein that has been designed for optimal expression in plant cells.

Expression cassettes and vectors containing these synthetic or artificial nucleotide sequences can be constructed and introduced into corn, cotton, and soybean plant cells in accordance with transformation methods and techniques which are known in the art. Transformed cells are regenerated into transformed plants that are observed to be expressing TIC5290. To test pesticidal activity, bioassays are performed in the presence of Lepidopteran, Coleopteran and Hemipteran pests.

TIC5290 protein-encoding sequences and sequences having a substantial percentage identity to TIC5290 can be identified using methods known to those of ordinary skill in the art such as polymerase chain reaction (PCR), thermal amplification and hybridization. For example, the protein TIC5290 can be used to produce antibodies that bind specifically to related proteins, and can be used to screen for and to find other protein members that are closely related.

Furthermore, nucleotide sequences encoding the TIC5290 toxin protein can be used as probes and primers for screening to identify other members of the class using thermal-cycle or isothermal amplification and hybridization methods. For example, oligonucleotides derived from the sequence as set forth as SEQ ID NO:3, can be used to determine the presence or absence of a TIC5290 transgene in a deoxyribonucleic acid sample derived from a commodity product. Given the sensitivity of certain nucleic acid detection methods that employ oligonucleotides, it is anticipated that oligonucleotides derived from the sequence as set forth as SEQ ID NO:3 can be used to detect a TIC5290 transgene in commodity products derived from pooled sources where only a fraction of the commodity product is derived from a transgenic plant containing SEQ ID NO:3. It is further recognized that such oligonucleotides can be used to introduce nucleotide sequence variation in SEQ ID NO:3. Such "mutagenesis" oligonucleotides are useful for identification of TIC5290 amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes under stringent hybridization conditions to the second nucleotide sequence. In such case, the second nucleotide sequence can be the nucleotide sequence presented as SEQ ID NO:1 or SEQ ID NO:3 under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding proteins related to TIC5290, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC5290. This application contemplates the use of these and other identification methods known to those of ordinary skill in the art, to identify TIC5290 protein-encoding sequences and sequences having a substantial percentage identity to TIC5290 protein-encoding sequences.

Methods of controlling insects, in particular Lepidoptera, or Coleoptera, or Hemiptera infestations of crop plants, with the TIC5290 protein are also disclosed in this application. Such methods can comprise growing a plant comprising an insect-, Coleoptera-, or Lepidoptera-, or Hemiptera-inhibitory amount of a protein of the TIC5290 toxin protein. In certain embodiments, such methods can further comprise any one or more of: (i) applying any composition comprising or encoding a TIC5290 toxin protein to a plant or a seed that gives rise to a plant; and (ii) transforming a plant or a plant cell that gives rise to a plant with a polynucleotide encoding a TIC5290 toxin protein. In general, it is contemplated that TIC5290 toxin protein can be provided in a composition, provided in a microorganism, or provided in a transgenic plant to confer insect inhibitory activity against Lepidopteran, Coleopteran or Hemipteran insects.

In certain embodiments, a recombinant nucleic acid molecule of TIC5290 toxin protein is the insecticidally active ingredient of an insect inhibitory composition prepared by culturing recombinant *Bacillus* or any other recombinant bacterial cell transformed to express a TIC5290 toxin protein under conditions suitable to express the TIC5290 toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC5290 can further comprise at least one additional polypeptide that exhibits insect inhibitory activity against the same Lepidopteran, Coleopteran or Hemipteran insect species, but which is different from the TIC5290 toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, axmi209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594(A2)), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in US7510878(B2), SEQ ID NO:2 and derivatives thereof as described in U.S. Pat. No. 7,812,129(B1); and the like.

Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-

0319092 A1), eHIPs (U.S. Patent Application Publication No. 2010/0017914), IP3 and variants thereof (U.S. Patent Publication 2012-0210462 A1), and $\overline{\omega}$-Hexatoxin-Hv1a (U.S. Patent Application Publication US2014-0366227 A1).

Such additional polypeptides for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran, or Lepidopteran, or Hemipteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC5290 pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery of TIC5290

This Example describes the discovery of pesticidal protein TIC5290.

A sequence encoding a novel *Bacillus thuringiensis* (Bt) pesticidal protein was identified, cloned, sequence confirmed and tested in insect bioassay. The pesticidal protein, TIC5290, presented herein as SEQ ID NO:1 (Bt coding sequence) and 2 (protein), was isolated from Bt strain EG6657. TIC5290 is a 937 amino acid long protein and was identified based on homology to known insecticidal protein toxins and through the use of Pfam analysis to cluster it with known insecticidal protein families. Bioinformatics analysis suggests TIC5290 is a pore-forming protein. A PA14 Pfam domain (PF07691) at amino acid residues 16 through 140 is likely involved with binding functions. This domain is followed by a Binary_toxB Pfam domain (PF03495) at amino acids 186 through 593 that might contribute to the formation of a beta-barrel transmembrane pore. The closest Bt toxin homolog to TIC5209 is the Vip4Aa protein, with a sequence identity of 56.9%, suggesting that TIC5290 represents a novel Vip4 subfamily.

PCR primers were designed to amplify a full length copy of the coding region for TIC5290 from total genomic DNA isolated from strain EG6657. The PCR amplicon also included the start and stop codons of the coding sequence.

The TIC5290 amplicon was cloned using methods known in the art into a Bt plasmid expression vector in operable linkage with a Bt expressible promoter that is on during sporulation of the *bacillus*. In addition, the amplicon was cloned into a vector used for protein expression in an *Escherichia coli* (*E. coli*) expression system. The resulting recombinant strains were observed to express recombinant protein.

Example 2

TIC5290 Demonstrates Coleopteran, Lepidopteran and Hemipteran Activity in Insect Bioassay This Example illustrates inhibitory activity exhibited by TIC5290 proteins against various species of Coleoptera, Lepidoptera and Hemiptera.

The novel pesticidal protein TIC5290 was expressed in Bt and *E. coli* and assayed for toxicity to various species of Coleoptera, Lepidoptera, Hemiptera, and Diptera. Preparations of each toxin from Bt and *E. coli* were assayed against the Coleopteran species *Leptinotarsa decemlineata* (Colorado potato beetle, CPB) and *Diabrotica virgifera virgifera* (Western Corn Rootworm, WCR). The toxin preparations were also assayed against the Lepidopteran species Corn earworm (CEW, *Helicoverpa zea*), European corn borer (ECB, *Ostrinia nubilalis*), Fall armyworm (FAW, *Spodop-*

*tera frugiperda*), Soybean looper (SBL, Chrysodeixis *includens*), Southwestern Corn Borer (SWC, *Diatraea grandiosella*), Tobacco budworm (TBW, *Heliothis virescens*), and Diamondback moth (DBM, (*lutella xylostella*). The toxin preparations were also assayed against the Hemipteran species Tarnished plant bug (TPB, *Lygus lineolaris*) and Western tarnished plant bug (WTP, *Lygus hesperus*); as well as the Dipteran species, Yellow fever mosquito (YFM, *Aedes aegypti*). Corn earworm (CEW, *Helicoverpa zea*) is also referred to as Soybean pod worm (SPW) and Cotton bowl worm (CBW).

Assay of proteins expressed in each of the vectors required different preparations added to an insect diet. For vectors using the promoter active during sporulation, a crystal/spore mixture was harvested after three days of growth in culture and used in an insect diet (generally applied to insect artificial diets and fed separately to various insects). Protein preparations derived from expression in *E. coli* were purified and also provided in an insect diet.

TIC5290 demonstrated activity against WCR, CEW, ECB, FAW, DBM and WTP, as shown in Table 2 below wherein "+" indicates activity.

TABLE 2

Bioassay activity of TIC5290 against Coleopteran, Lepidopteran, Hemipteran and Dipteran insect pests.

| Insect | Diet Bioassay |
|---|---|
| WCR | + |
| CPB | − |
| CEW | + |
| ECB | + |
| FAW | + |
| SBL | − |
| SWC | − |
| TBW | − |
| DBM | + |
| TPB | − |
| WTP | + |
| YFM | − |

Example 3

Design of Synthetic Coding Sequences Encoding TIC5290 for Expression in Plant Cells Synthetic or artificial coding sequences were constructed for use in expression of TIC5290 in plants, and were cloned into a binary plant transformation vector, and used to transform plant cells. The synthetic nucleic acid sequences were synthesized according to methods generally described in U.S. Pat. No. 5,500,365, avoiding certain inimical problem sequences such as ATTTA and A/T rich plant polyadenylation sequences while preserving the amino acid sequence of the native Bt protein. The synthetic coding sequence for the TIC5290 pesticidal protein is presented as SEQ ID NO:3 and encodes the protein presented as SEQ ID NO:2.

Example 4

Expression Cassettes for Expression of TIC5290 in Plant Cells

A variety of plant expression cassettes were designed with the sequences as set forth in SEQ ID NO:3. Such expression cassettes are useful for transient expression in plant protoplasts or transformation of plant cells. Typical expression cassettes were designed with respect to the eventual placement of the protein within the plant cell. For plastid targeted protein the synthetic TIC5290 pesticidal protein coding sequence was operably linked in frame with a chloroplast targeting signal peptide coding sequence. The resulting plant transformation vectors comprise a first transgene cassette for expression of the pesticidal protein which comprises a constitutive promoter, operably linked 5' to a leader, operably linked 5' to an intron (or optionally no intron), operably linked 5' to a synthetic coding sequence encoding a plastid targeted or untargeted TIC5290 protein, which is in turn operably linked 5' to a 3' UTR and; a second transgene cassette for the selection of transformed plant cells using glyphosate or antibiotic selection. All of the elements described above were arranged contiguously often with additional sequence provided for the construction of the expression cassette such as restriction endonuclease sites or ligation independent cloning sites.

Example 5

TIC5290 Provides Efficacious Resistance to Western Corn Rootworm (*Diabrotica virgifera virgifera*) when Expressed in Stably Transformed Corn Plants This Example illustrates the inhibitory activity exhibited by TIC5290 against Coleoptera such as corn rootworm when expressed in plants and provided as a diet to the respective insect pest.

Binary plant transformation vectors comprising transgene cassettes designed to express both plastid targeted and untargeted TIC5290 pesticidal proteins were cloned using methods known in the art. The resulting vectors were used to stably transform corn plants. Single T-DNA insertion events were selected and grown. Pesticidal activity were assayed against the Coleopteran pest Western Corn Rootworm (*Diabrotica virgifera virgifera*) feeding on the roots of the stably transformed corn plants.

$R_0$ stably transformed plants were used to assay for Coleopteran resistance as well as generating $F_1$ progeny. Multiple single copy events were selected from each binary vector transformation. A portion of those events arising from each binary vector transformation were used in the Coleopteran assay, while another portion of events were used to generate $F_1$ progeny for further testing.

The $R_0$ assay plants were transplanted to eight inch pots. The plants were inoculated with eggs from Western Corn Rootworm (*Diabrotica virgifera virgifera*, WCR). The eggs were incubated for approximately ten days prior to inoculation to allow hatching to occur four days after inoculation to ensure a sufficient number of larvae survive and are able to attack the corn roots. The transformed plants were inoculated at approximately V2 to V3 stage. The plants were grown after infestation for approximately twenty eight days. The plants were removed from the pots with the roots being carefully washed to remove all soil. The damage to the roots was assessed using a damage rating scale of 1-5 as presented in Table 3 below. Comparison was also made to the negative control to assure the assay has been performed properly. Low root damage scores indicate resistance conferred by the TIC5290 protein to the Coleopteran pest. Multiple $R_0$ events for each binary vector transformation were used in the WCR assay. Many of the $R_0$ events expressing both plastid targeted and untargeted TIC5290 demonstrated resistance to WCR determined by the root damage rating scores when compared to transgenic controls.

TABLE 3

| $R_0$ root damage rating scores. | |
|---|---|
| Root Damage Score | Description |
| 1 | No visible feeding |
| 2 | Some feeding; no pruning |
| 3 | Pruning of at least one root |
| 4 | Entire node pruned |
| 5 | More than one node pruned |

A portion of the $R_0$ stably transformed events arising from each binary vector transformation were used to produce $F_1$ progeny. The $R_0$ stably transformed plants were allowed to self-fertilize, producing $F_1$ progeny. The $F_1$ seed was planted. Heterozygous plants were identified through molecular methods known in the art and used for assay against WCR, as well as ELISA expression measurements of TIC5290 toxin protein. A portion of the heterozygous $F_1$ progeny from each event was used for insect assay, while another portion was used to measure TIC5290 expression.

Eggs from Western Corn Rootworm (*Diabrotica virgifera virgifera*, WCR) were incubated for approximately ten days to allow hatching within four days after inoculation. The plants were inoculated at approximately V2 to V3 stage. For WCR, each pot was inoculated with about two thousand eggs. The plants were grown after infestation for approximately twenty eight days. The plants were removed from the pots with the roots being carefully washed to remove all soil. The damage to the roots was assessed using a damage rating scale of 0-3 as presented in Table 4 below. Comparison was made to the negative control to assure the assay has been performed properly. Low root damage scores indicated resistance conferred by the TIC5290 protein to the Coleopteran pest. Many of the $F_1$ events demonstrated efficacious resistance to WCR when compared to the controls. FIG. 1 depicts the average root damage rating for several events for TIC5290 when expressed in F1 corn plants regardless of whether the protein is targeted to the chloroplast.

TABLE 4

| $F_1$ root damage rating scores. | |
|---|---|
| Root Damage Score | Description |
| 0 | No visible feeding |
| 0.01-0.09 | Feeding scars and tracks |
| 0.1-0.9 | Root pruning, but less than a full node |
| 1.0-1.9 | At least a full node (or equivalent) destroyed to within 1.5 inches of plant |
| 2.0-2.9 | Two or more nodes gone |
| 3 | Three or more nodes gone |

Example 5

Assay of Activity of TIC5290 Against Lepidopteran Pests when Expressed in Stably Transformed Corn, Soybean, or Cotton Plants Binary plant transformation vectors comprising transgene cassettes designed to express both plastid targeted and untargeted TIC5290 pesticidal protein are cloned using methods known in the art.

Corn, soybean, or cotton is transformed with the binary transformation vectors described above using an *Agrobacterium*-mediated transformation method. The transformed cells are induced to form plants by methods known in the art. Bioassays using plant leaf disks are performed analogous to those described in U.S. Pat. No. 8,344,207. A non-transformed corn, soybean, or cotton plant is used to obtain tissue to be used as a negative control. Multiple transformation events from each binary vector are assessed against Lepidopteran pests such as, but not limited to, Corn earworm (CEW, *Helicoverpa zea*), European corn borer (ECB, *Ostrinia nubilalis*), Fall armyworm (FAW, *Spodoptera frugiperda*), Soybean looper (SBL, *Chrysodeixis includens*), Southwestern Corn Borer (SWCB, *Diatraea grandiosella*), Tobacco budworm (TBW, *Heliothis virescens*), and Diamondback moth (DBM, (*lutella xylostella*). Those insects demonstrating stunting and/or mortality in the insect bioassay are determined to be susceptible to the effects of the TIC5290 insect toxin.

Example 6

Assay of Activity Against Hemipteran Pests Using Stably Transformed Cotton Plants Expressing TIC5290

Binary plant transformation vectors comprising transgene cassettes designed to express both plastid targeted and untargeted TIC5290 pesticidal proteins are cloned using methods known in the art. The resulting vectors are used to stably transform cotton plants. Pesticidal activity is assayed against Hemipteran pests feeding on the stably transformed cotton plants.

The binary vectors described previously in Example 3 in which plastid targeted and untargeted TIC5290 is expressed are used to stably transform cotton plants. Single T-DNA insertion events are selected and grown. The $R_0$ stably transformed plants are allowed to self-fertilize, producing $R_1$ progeny.

$R_1$ transgenic seeds comprising expression cassettes for TIC5290 are sown in 10 inch pots along with seeds corresponding to a non-transgenic control. Plants are maintained in an environment chamber with a photoperiod of sixteen hours of light at thirty two degrees Celsius and eight hours of dark at twenty three degrees Celsius, and a light intensity between eight hundred to nine hundred micro-Einsteins. At forty to forty five days after planting, the individual plants are enclosed in a cage made from breathable plastic “pollination” sheets (Vilutis and Company Inc, Frankfort, Ill.). The sheet sleeves are secured to the main stem just above the soil surface using a Velcro® tie. Two pairs of sexually mature male and female *Lygus lineolaris* or *Lygus hesparus* adults (six days old) from laboratory culture are collected into a fourteen milliliter round-bottom plastic tube (Becton Dickson Labware, Franklin Lakes, N.J.) and used for each plant. The adults are released into each individual cage through a small slit on the cage side and then the cage is securely closed ensuring the insects will not escape. The insects are allowed to mate and the plants are kept in the cage for twenty one days. After twenty one days, the plants are then cut below the cages and moved to a laboratory where the insects are collected for each plant and counted. Before opening the cage, the plants are vigorously shaken to ensure all of the insects fall off from their feeding sites to the base of the cage. Then the cage base is opened and all plant material removed and placed on a black sheet. The insects are collected using an aspirator. The plant is then thoroughly inspected to recover any remaining insects. The numbers of insects and their developmental stage are recorded for each plant. The insect counts are divided into several groups based upon maturity of the *Lygus*; nymphs up to $3^{rd}$ instar, $4^{th}$ instar, $5^{th}$ instar and adults. Transgenic cotton plants demonstrating reduced numbers of nymphs and adults relative to the untransformed cotton control plants demonstrate resistance conferred to the Hemipteran pests through expression of the TIC5290 toxin protein.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein that comprises the amino acid sequence of SEQ ID NO:2.

2. A vector comprising the recombinant nucleic acid molecule of claim 1, wherein said vector is selected from the group consisting of a plasmid, phagemid, bacmid, cosmid, and a bacterial or yeast artificial chromosome.

3. The recombinant nucleic acid molecule of claim 1, wherein the promoter functions to express the pesticidal protein in a plant.

4. A host cell comprising the recombinant nucleic acid molecule of claim 1, wherein said host cell is selected from the group consisting of a bacterial and a plant cell.

5. The host cell of claim 4, wherein the bacterial host cell is from a genus of bacteria selected from the group consisting of: *Agrobacterium, Rhizobium, Bacillus, Brevibacillus, Escherichia, Pseudomonas, Klebsiella, Pantoea*, and *Erwinia*.

6. The host cell of claim 5, wherein the *Bacillus* species is *Bacillus cereus* or *Bacillus thuringiensis*, said *Brevibacillus* is *Brevibacillus laterosperus*, or said *Escherichia* is *Escherichia coli*.

7. The host cell of claim 4, wherein said plant cell is a dicotyledonous or a monocotyledonous plant cell.

8. The host cell of claim 7, wherein said plant host cell is selected from the group consisting of an alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

9. A plant or part thereof comprising the recombinant nucleic acid molecule of claim 1.

10. The plant or part thereof of claim 9, wherein said plant is a monocot plant or a dicot plant.

11. The plant or part thereof of claim 9, wherein the plant is selected from the group consisting of an alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

12. A seed of the plant of claim 9, wherein said seed comprises said recombinant nucleic acid molecule.

13. An insect inhibitory composition comprising the recombinant nucleic acid molecule of claim 1 and the pesticial protein encoded by the polynucleotide segment.

14. The insect inhibitory composition of claim 13, further comprising a nucleotide sequence encoding at least one other pesticidal agent that is different from said pesticidal protein.

15. The insect inhibitory composition of claim 14, wherein said at least one other pesticidal agent is selected from the group consisting of an insect inhibitory protein, an insect inhibitory dsRNA molecule, and an ancillary protein.

16. The insect inhibitory composition of claim 14, wherein said at least one other pesticidal agent exhibits activity against one or more pest species of the orders Lepidoptera, Coleoptera, or Hemiptera.

17. The insect inhibitory composition of claim 16, wherein said at least one other pesticidal protein is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z, AXMI-225z, AXMI-238, AXMI-270, AXMI-279, AXMI-345, AXMI-335, AXMI-R1, IP3, DIG-3, DIG-5, DIG-10, DIG-657 and a DIG-11.

18. The insect inhibitory composition of claim 13, defined as comprising a plant cell that expresses said recombinant nucleic acid molecule.

19. A commodity product produced from the plant or part thereof of claim 9, wherein the commodity product comprises a detectable amount of said recombinant nucleic acid molecule or a pesticidal protein encoded thereby.

20. The commodity product of claim 19, selected from the group consisting of commodity corn bagged by a grain handler, corn flakes, corn cakes, corn flour, corn meal, corn syrup, corn oil, corn silage, corn starch, corn cereal, and the like, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

21. A method of producing seed, said method comprising:

a. planting at least a first seed according to claim 12;

b. growing a plant from the seed; and c. harvesting seed from the plant, wherein said harvested seed comprises said recombinant nucleic acid molecule.

22. A plant resistant to insect infestation, wherein the cells of said plant comprise the recombinant nucleic acid molecule of claim 1.

23. A method for controlling a Coleopteran or Lepidopteran or Hemipteran species pest or pest infestation, said method comprising contacting the pest with the insect inhibitory composition of claim 13.

24. The method of claim 23, wherein the pest is a Western Corn Rootworm.

25. The method of claim 23, wherein the pest is a Corn earworm, a Diamondback moth, a Fall armyworm, or a European corn borer.

26. The method of claim 23, wherein the pest is a Western tarnished plant bug.

* * * * *

SEQUENCE LISTING

```
<160> NUMBER OF SEQ ID NOS: 3

<210> SEQ ID NO 1
<211> LENGTH: 2814
<212> TYPE: DNA
<213> ORGANISM: Bacillus thuringiensis
<220> FEATURE:
<221> NAME/KEY: misc_feature
<222> LOCATION: (1)..(2814)
<223> OTHER INFORMATION: DNA sequence derived from Bt strain EG6657
      encoding TIC5290.

<400> SEQUENCE: 1

atgcaaaata tcgtttcttc aaaaagcgaa caggcgacgg tcattggatt agttggtttt     60

tactttaaag atagtacatt taaagaattg atgtttatcc aggtgggcga aaaaagtaac    120

ttaatgaata aagcgagaat aaacacagat gcgcaacaaa ttcaatctat acgatggatg    180

gggaatttga agtctcccca aacgggagag tataggcttt ctacatcttc cgatgaaaat    240

gtaattctgc aaataaatgg cgaaacagtc attaatcaag ctagtataca aaaaaacctt    300

aaactagaag caaatcaggt atatgaaatc aagattgagt atcgtaatac atcgaataca    360

ttaccagatt tgcagttatt ctggtcaatg aacaatgcgc aaaaagaaca aatcccggag    420

aaatatatac tctctccaaa tttctctgaa aaagcaaatt cacttgccga aaaagaaaca    480

caaagtttct ttccaaatta taatttattt gatagacaac aagaaaatgg agaaaaacaa    540

tccatgtcta ctcctgtaga cacagataat gattgtattc cagatgaatg ggaagaaaag    600

ggatatacat ttagaaatca acaaattgtg ccatggaatg atgcatatag tgctgaaggc    660

tacaaaaaat atgtctcaaa tccttatcat gcacgaacag taaaagatcc ttatacagat    720

tttgaaaagg taacaggaca tatgccggca gcgacgaaat acgaagcaag agatccacta    780

gtagctgcgt atccatcggt tggagttgga atggaaaaac ttcatttttc taaaaatgat    840

actgtaactg agggaaatgc tgacacaaaa tctaaaacaa ccacaaaaac agatacgacc    900

acaaatactg tagagattgg tggatcgctc ggcttttcag ataaaggctt ttctttttca    960

atttcaccaa aatacacaca ttcttggagt agtagcacat ccgttgcaga tacggacagt   1020

acaacatggt cttcacaaat tggaattaac acggcagaaa gagcatattt aaatgcaaat   1080

gttcgttatt acaatggtgg aacggcacct atttatgatc taaaaccgac aacaaatttt   1140

gtcttccaaa attcaggtga ttccattact acgataacgg ctggacctaa tcaaattgga   1200

aatagtctag gtgcaggcga tacctatccg caaaaaggac aggccccgat ttcattagat   1260

aaagcaaatg aggctggtac agtaaaaatt gcaatcaatg ctgaacaatt agataaaata   1320
```

-continued

```
caagctggta cagaaatatt aaatatagaa actacgcaaa atagaggaca atatggaatt   1380
ttagatgaaa aaggtcaagt aattccaggt ggagaatggg atccgattcg aacaaatatt   1440
gatgcggtct ctggatcact cacattaaat cttggtacag ggaaagatag tctcgaacga   1500
agagtagctg caaaaaatat gaatgatcca gaagataaaa cacctgaaat tacaatcaaa   1560
gaagcaatca aaaaagcgtt taatgcacaa gaaaaagatg gtagattata ctatacggat   1620
caaggcgaaa aagatatatt tatcgatgaa ccttctatta atttaatcac agatgaaaat   1680
acaaaaaaag aaattgagcg ccaattaaat caaatgccag gtaaaacagt atatgatgta   1740
aaatggaaac gcgggatgaa gatcacactt catgtaccaa taaagtacta tgatttcgaa   1800
acctccgaaa atctatggta ttatacatac caagaaagcg gaggatatac gggtaaaaaa   1860
cgaggaagaa ttggtacaga tgggcatggg actgcgatgt caaatccaca attaaaaccg   1920
tatacaagtt atacggtgcg tgcatacgta cgaacagcat caacaacggg tagtaatgaa   1980
gttgtatttt atgcagataa tagctccggg aatggacaag gtgcaaaagt aagtggaaaa   2040
gtcacaggtg gtaaatggaa aatagcggaa ttttctttta atactttttaa caacccagag   2100
tattttaaaa taatcggttt gaaaaataac gggaatgcta atctccattt tgatgatgta   2160
tctgtaatag agtggaaaac aaatgaaaat cttcaaaaaa aacatatatt tgaaaaatgg   2220
agttttggtt caaatgatga gatggtgata ggtgcaacgt ttactcgtgt tccaagttcg   2280
aagattcgat accaatggaa aataaatggt aggttgggaa gtataatacc tgcaccgcca   2340
ttagacgcta atggtaaaag aactgtaacc tatggatcaa ttactgctat tactcccatg   2400
gaattatatg ctgtagatga aaaaaatgac aacctaaaag taaaagtagc tgaactcggc   2460
gagagtgaga ttgaaaaagt aatgatagat gcacataaat tttccgggtg gtggtattta   2520
tctgaaaacc caaacctgta tagtggtctt agtttataca aattacctga tatattttat   2580
aataacgtat cttcttataa aattcgagtg aatggaaaaa aagttcaaac agtctcaaaa   2640
ccaagcccat ttctttttca gataacgttt aatctaaaaa atcctaatgg tggcacttat   2700
cctactaaag atgcatcagt cgaattatgg gctacagtag gtggaaaaga tttaaaggtg   2760
ttgcataagt ggattcaaaa aagcgatgtt atgtacagtc agactaataa ttaa         2814
```

<210> SEQ ID NO 2
<211> LENGTH: 937
<212> TYPE: PRT
<213> ORGANISM: Bacillus thuringiensis
<220> FEATURE:
<221> NAME/KEY: MISC_FEATURE
<222> LOCATION: (1)..(937)
<223> OTHER INFORMATION: Amino acid sequence of TIC5290.

<400> SEQUENCE: 2

```
Met Gln Asn Ile Val Ser Ser Lys Ser Glu Gln Ala Thr Val Ile Gly
1               5                   10                  15

Leu Val Gly Phe Tyr Phe Lys Asp Ser Thr Phe Lys Glu Leu Met Phe
            20                  25                  30

Ile Gln Val Gly Glu Lys Ser Asn Leu Met Asn Lys Ala Arg Ile Asn
        35                  40                  45

Thr Asp Ala Gln Gln Ile Gln Ser Ile Arg Trp Met Gly Asn Leu Lys
    50                  55                  60

Ser Pro Gln Thr Gly Glu Tyr Arg Leu Ser Thr Ser Ser Asp Glu Asn
65                  70                  75                  80

Val Ile Leu Gln Ile Asn Gly Glu Thr Val Ile Asn Gln Ala Ser Ile
                85                  90                  95
```

-continued

```
Gln Lys Asn Leu Lys Leu Glu Ala Asn Gln Val Tyr Glu Ile Lys Ile
            100                 105                 110

Glu Tyr Arg Asn Thr Ser Asn Thr Leu Pro Asp Leu Gln Leu Phe Trp
        115                 120                 125

Ser Met Asn Asn Ala Gln Lys Glu Gln Ile Pro Glu Lys Tyr Ile Leu
    130                 135                 140

Ser Pro Asn Phe Ser Glu Lys Ala Asn Ser Leu Ala Glu Lys Glu Thr
145                 150                 155                 160

Gln Ser Phe Phe Pro Asn Tyr Asn Leu Phe Asp Arg Gln Gln Glu Asn
                165                 170                 175

Gly Glu Lys Gln Ser Met Ser Thr Pro Val Asp Thr Asp Asn Asp Cys
            180                 185                 190

Ile Pro Asp Glu Trp Glu Glu Lys Gly Tyr Thr Phe Arg Asn Gln Gln
        195                 200                 205

Ile Val Pro Trp Asn Asp Ala Tyr Ser Ala Glu Gly Tyr Lys Lys Tyr
    210                 215                 220

Val Ser Asn Pro Tyr His Ala Arg Thr Val Lys Asp Pro Tyr Thr Asp
225                 230                 235                 240

Phe Glu Lys Val Thr Gly His Met Pro Ala Ala Thr Lys Tyr Glu Ala
                245                 250                 255

Arg Asp Pro Leu Val Ala Ala Tyr Pro Ser Val Gly Val Gly Met Glu
            260                 265                 270

Lys Leu His Phe Ser Lys Asn Asp Thr Val Thr Glu Gly Asn Ala Asp
        275                 280                 285

Thr Lys Ser Lys Thr Thr Thr Lys Thr Asp Thr Thr Thr Asn Thr Val
    290                 295                 300

Glu Ile Gly Gly Ser Leu Gly Phe Ser Asp Lys Gly Phe Ser Phe Ser
305                 310                 315                 320

Ile Ser Pro Lys Tyr Thr His Ser Trp Ser Ser Ser Thr Ser Val Ala
                325                 330                 335

Asp Thr Asp Ser Thr Thr Trp Ser Ser Gln Ile Gly Ile Asn Thr Ala
            340                 345                 350

Glu Arg Ala Tyr Leu Asn Ala Asn Val Arg Tyr Tyr Asn Gly Gly Thr
        355                 360                 365

Ala Pro Ile Tyr Asp Leu Lys Pro Thr Thr Asn Phe Val Phe Gln Asn
    370                 375                 380

Ser Gly Asp Ser Ile Thr Thr Ile Thr Ala Gly Pro Asn Gln Ile Gly
385                 390                 395                 400

Asn Ser Leu Gly Ala Gly Asp Thr Tyr Pro Gln Lys Gly Gln Ala Pro
                405                 410                 415

Ile Ser Leu Asp Lys Ala Asn Glu Ala Gly Thr Val Lys Ile Ala Ile
            420                 425                 430

Asn Ala Glu Gln Leu Asp Lys Ile Gln Ala Gly Thr Glu Ile Leu Asn
        435                 440                 445

Ile Glu Thr Thr Gln Asn Arg Gly Gln Tyr Gly Ile Leu Asp Glu Lys
    450                 455                 460

Gly Gln Val Ile Pro Gly Gly Glu Trp Asp Pro Ile Arg Thr Asn Ile
465                 470                 475                 480

Asp Ala Val Ser Gly Ser Leu Thr Leu Asn Leu Gly Thr Gly Lys Asp
                485                 490                 495

Ser Leu Glu Arg Arg Val Ala Ala Lys Asn Met Asn Asp Pro Glu Asp
            500                 505                 510
```

-continued

```
Lys Thr Pro Glu Ile Thr Ile Lys Glu Ala Ile Lys Lys Ala Phe Asn
        515                 520                 525

Ala Gln Glu Lys Asp Gly Arg Leu Tyr Tyr Thr Asp Gln Gly Glu Lys
    530                 535                 540

Asp Ile Phe Ile Asp Glu Pro Ser Ile Asn Leu Ile Thr Asp Glu Asn
545                 550                 555                 560

Thr Lys Lys Glu Ile Glu Arg Gln Leu Asn Gln Met Pro Gly Lys Thr
                565                 570                 575

Val Tyr Asp Val Lys Trp Lys Arg Gly Met Lys Ile Thr Leu His Val
            580                 585                 590

Pro Ile Lys Tyr Tyr Asp Phe Glu Thr Ser Glu Asn Leu Trp Tyr Tyr
        595                 600                 605

Thr Tyr Gln Glu Ser Gly Gly Tyr Thr Gly Lys Lys Arg Gly Arg Ile
    610                 615                 620

Gly Thr Asp Gly His Gly Thr Ala Met Ser Asn Pro Gln Leu Lys Pro
625                 630                 635                 640

Tyr Thr Ser Tyr Thr Val Arg Ala Tyr Val Arg Thr Ala Ser Thr Thr
                645                 650                 655

Gly Ser Asn Glu Val Val Phe Tyr Ala Asp Asn Ser Ser Gly Asn Gly
            660                 665                 670

Gln Gly Ala Lys Val Ser Gly Lys Val Thr Gly Gly Lys Trp Lys Ile
        675                 680                 685

Ala Glu Phe Ser Phe Asn Thr Phe Asn Asn Pro Glu Tyr Phe Lys Ile
    690                 695                 700

Ile Gly Leu Lys Asn Asn Gly Asn Ala Asn Leu His Phe Asp Asp Val
705                 710                 715                 720

Ser Val Ile Glu Trp Lys Thr Asn Glu Asn Leu Gln Lys Lys His Ile
                725                 730                 735

Phe Glu Lys Trp Ser Phe Gly Ser Asn Asp Glu Met Val Ile Gly Ala
            740                 745                 750

Thr Phe Thr Arg Val Pro Ser Ser Lys Ile Arg Tyr Gln Trp Lys Ile
        755                 760                 765

Asn Gly Arg Leu Gly Ser Ile Ile Pro Ala Pro Pro Leu Asp Ala Asn
    770                 775                 780

Gly Lys Arg Thr Val Thr Tyr Gly Ser Ile Thr Ala Ile Thr Pro Met
785                 790                 795                 800

Glu Leu Tyr Ala Val Asp Glu Lys Asn Asp Asn Leu Lys Val Lys Val
                805                 810                 815

Ala Glu Leu Gly Glu Ser Glu Ile Glu Lys Val Met Ile Asp Ala His
            820                 825                 830

Lys Phe Ser Gly Trp Trp Tyr Leu Ser Glu Asn Pro Asn Leu Tyr Ser
        835                 840                 845

Gly Leu Ser Leu Tyr Lys Leu Pro Asp Ile Phe Tyr Asn Asn Val Ser
    850                 855                 860

Ser Tyr Lys Ile Arg Val Asn Gly Lys Lys Val Gln Thr Val Ser Lys
865                 870                 875                 880

Pro Ser Pro Phe Leu Phe Gln Ile Thr Phe Asn Leu Lys Asn Pro Asn
                885                 890                 895

Gly Gly Thr Tyr Pro Thr Lys Asp Ala Ser Val Glu Leu Trp Ala Thr
            900                 905                 910

Val Gly Gly Lys Asp Leu Lys Val Leu His Lys Trp Ile Gln Lys Ser
        915                 920                 925

Asp Val Met Tyr Ser Gln Thr Asn Asn
```

930 935

<210> SEQ ID NO 3
<211> LENGTH: 2814
<212> TYPE: DNA
<213> ORGANISM: Artificial
<220> FEATURE:
<223> OTHER INFORMATION: Synthetic coding sequence encoding TIC5290
designed for expression in plants.

<400> SEQUENCE: 3
atgcagaaca ttgtctcctc caagagtgag caagcgacgg tcatcggcct ggtcggcttc 60
tacttcaagg actcaacctt caaggagctc atgttcatcc aggtgggcga gaagtccaac 120
ctcatgaaca aggctcgcat caacacggac gcccagcaga tccagtccat tcggtggatg 180
ggcaacctga agagcccgca gaccggcgag taccgcctct ccacatcctc cgacgagaac 240
gtaatcctcc agatcaatgg cgagacggtc atcaaccagg cgagcatcca gaagaacctc 300
aaactagagg caaaccaggt ctacgagatt aagatcgagt acaggaacac ctccaacacc 360
ctgccggacc tacagctctt ctggtcgatg aacaacgcgc agaaggaaca gatcccggag 420
aagtacatac tgagcccgaa tttcagcgag aaggcgaact ctctcgcgga gaaggagacc 480
cagagcttct tcccgaacta caacctcttc gaccgccagc aagagaacgg cgagaagcag 540
tcgatgtcca cgccggtgga caccgacaac gactgcatcc ctgatgaatg ggaagagaaa 600
ggatacacct tccgtaacca gcagatcgtg ccgtggaacg acgcctacag tgcagaaggc 660
tacaagaagt acgtgagcaa cccttaccac gcccgtacgg tcaaagaccc gtacaccgac 720
ttcgagaagg tgactgggca catgcccgct gctacgaagt atgaggcgcg cgatcctcta 780
gtggccgcct atccctccgt tggcgtcgga atggagaagc tccacttcag caagaacgat 840
acggtgacgg agggcaacgc ggatacaaag agcaagacta caactaagac cgacaccacg 900
accaacaccg tcgagatcgg cggcagcctg ggcttcagcg acaagggctt cagtttctca 960
atctcaccaa agtacaccca cagctggtcg tcgtccacaa gtgtggccga caccgactct 1020
actacctgga gttcgcagat agggatcaac actgccgaga gggcgtatct caacgcgaac 1080
gtgcgctatt acaatggtgg caccgcgccc atctacgacc tgaagccgac caccaacttc 1140
gtcttccaga actcaggcga cagcatcacc acgatcaccg ccggccctaa ccagatcggc 1200
aactcgctcg gtgccggcga cacctatccg cagaagggcc aggctcctat ctccctagac 1260
aaggccaacg aggcgggcac cgtgaagata gcgatcaacg ccgagcagct ggacaagatc 1320
caggcgggca cggagattct caacatcgag actacgcaga accgcggcca gtacggtatc 1380
ctcgacgaga aaggccaggt gatacccgga ggcgagtggg acccgatccg gacaaacatt 1440
gacgctgtca gtgggagcct tactcttaac ctcggcacgg gcaaggatag cctcgagcgc 1500
cgggtcgcgg cgaagaacat gaacgatccg gaggacaaga ctccggagat caccatcaag 1560
gaggccatca agaaggcgtt taacgctcag gagaaggacg gcagactgta ctacacggac 1620
cagggtgaga aggacatctt cattgatgag ccttccatca acctcatcac ggacgagaac 1680
acgaagaaag aaatcgagcg ccagctgaac cagatgcccg gcaagacggt gtacgacgtg 1740
aagtggaagc gcggcatgaa gatcacgcta cacgtcccga tcaagtacta cgacttcgag 1800
acctcagaga acctgtggta ctacacctac caagaatccg gaggctacac cggcaagaag 1860
cgcgggcgga tcggcactga cgggcacggc acggcgatgt caaacccgca gctgaagcca 1920
tacacctcct acactgtgcg ggcgtacgtg cgcaccgcca gcaccactgg gagcaacgag 1980

-continued

| | |
|---|---|
| gtcgtcttct acgctgacaa cagctccggc aacgggcaag gcgcgaaggt ttccgggaag | 2040 |
| gtgaccggcg ggaagtggaa gatagcggag ttctccttca acacgttcaa taaccctgaa | 2100 |
| tacttcaaga tcatcggcct gaagaataac gggaacgcca acctgcactt cgacgatgtc | 2160 |
| tccgtgatcg agtggaagac caacgagaac ctgcagaaga aacacatctt tgagaagtgg | 2220 |
| tccttcggct ccaacgacga gatggtgatc ggtgccacgt tcactcgcgt gccgagtagc | 2280 |
| aagatccgat accagtggaa gatcaacggc cgcctcggta gcatcatccc tgcgccgcct | 2340 |
| ctggacgcca acgggaagcg gacggtgacg tacggcagca tcactgcgat cacgcctatg | 2400 |
| gagctctacg ccgttgacga gaagaacgac aacctcaaag tgaaagtcgc tgagcttggc | 2460 |
| gagtccgaga tcgagaaagt tatgatcgac gcccacaaat tctcaggctg gtggtatctc | 2520 |
| tcagagaatc caaacctgta ctccggcctc agcctgtaca agctgcccga catcttctac | 2580 |
| aacaacgtgt cgagctacaa gatccgcgtg aacggcaaga aggtccagac cgtcagcaag | 2640 |
| ccgagcccgt tcttgttcca gattacgttt aatctcaaga accctaacgg cgggacctac | 2700 |
| ccgacgaaag atgctagcgt agagctctgg gcgacggtcg gcgggaagga cctgaaggtg | 2760 |
| ctacacaagt ggattcagaa gtcggatgtc atgtacagcc agaccaacaa ctga | 2814 |